(12) United States Patent
Krause

(10) Patent No.: US 6,503,249 B1
(45) Date of Patent: Jan. 7, 2003

(54) TARGETING DEVICE FOR AN IMPLANT

(76) Inventor: William R. Krause, 820 Gilliams Mountain Rd., Charlottesville, VA (US) 22903

( * ) Notice: Subject to any disclaimer, the term of this patent is extended or adjusted under 35 U.S.C. 154(b) by 83 days.

(21) Appl. No.: 09/592,771

(22) Filed: Jun. 13, 2000

Related U.S. Application Data

(63) Continuation-in-part of application No. 09/013,827, filed on Jan. 27, 1998, now Pat. No. 6,074,394.

(51) Int. Cl.[7] .......................... A61B 17/56; A61B 17/58; A61F 5/00
(52) U.S. Cl. ............................. 606/62; 606/86; 606/87; 606/96
(58) Field of Search ........................... 623/16.11, 17.11, 623/11.11; 606/86, 96, 97, 98, 87, 99, 62, 59

(56) References Cited

U.S. PATENT DOCUMENTS

| | | | | |
|---|---|---|---|---|
| 4,394,831 A | * | 7/1983 | Egli et al. ...................... | 89/41 |
| 4,621,628 A | * | 11/1986 | Brudermann ................. | 128/92 |
| 4,849,692 A | * | 7/1989 | Blood .......................... | 324/208 |
| 5,411,503 A | * | 5/1995 | Hollstein et al. .............. | 606/86 |
| 5,478,343 A | * | 12/1995 | Ritter ........................... | 606/97 |
| 5,514,145 A | * | 5/1996 | Durham et al. ................ | 606/96 |
| 5,584,838 A | * | 12/1996 | Rona et al. .................... | 606/96 |
| 5,787,886 A | * | 8/1998 | Kelly et al. .............. | 128/653.1 |

* cited by examiner

Primary Examiner—Corrine McDermott
Assistant Examiner—Alvin Stewart
(74) Attorney, Agent, or Firm—Sheldon H. Parker

(57) ABSTRACT

The invention discloses a two- or three-axis transmitter positioner driven by a pulsed DC current, external to the patient, coupled with three- or two-axis receivers positioned internal and/or external to the implant. The receivers are sensitive to a transmitted DC magnetic field emanating from the activated transmitter. Receiver signal processing electronics control the receiver and serve to convert its output to a format suitable for processing by a digital computer in conjunction with a method for processing received signals so as to thereby develop position and orientation data of the transverse locking holes or pin placement. Such data then can be graphically displayed to the user so as to guide the user for accurate alignment of a drill bit with the transverse holes in the implanted device.

11 Claims, 12 Drawing Sheets

TARGETING DEVICE FOR AN IMPLANT

This application is a continuation-in-part (CIP) of U.S. application Ser. No. 09/013,827 filed Jan 27, 1998, now U.S. Pat. No. 6,074,394.

FIELD OF INVENTION

The invention relates to the positioning of a first element, relative to a second device, through the use of direct current magnetic field generating and receiving devices, and more particularly, to the installation of orthopaedic implants. More particularly, it relates to an improvement over existing devices used for locating holes in an implanted prosthesis so that a screw or pin for interlocking the prosthesis either with itself or with the surrounding bone can be accurately installed. The invention specifically relates to a positioner or aiming (targeting) device for locking screw or pins for such orthopedic hardware which employs pulsed direct current (DC) transmitted signals to enable precise positioning of such screws or pins.

BACKGROUND OF THE INVENTION

Various intramedullary nails and targeting devices for interlocking the intramedullary nail to the surrounding bone, particularly for the use in repairing the femur, are known in the prior art. One targeting method that is capable of providing precise locating of the holes distally uses x-ray techniques, but long periods of x-ray exposure are required and the need to move the x-ray equipment in and out of position to check the screw or pin locations means that there is a risk of a loss of alignment each time the equipment is moved. Patents of interest in this field include U.S. Pat. No. 5,537,453 (Williams et.al.); U.S. Pat. No. 5,478,343 (Ritter); U.S. Pat. No. 5,426,687 (Goodall et al); U.S. Pat. No. 5,178,621 (Cook, et. al.); U.S. Pat. No. 5,031,203 (Trecha); U.S. Pat. No. 5,030,222 (Calandruccio et al); U.S. Pat. No. 5,013,317 (Cole et al); and others as cited in the above patents. As a consequence of these radiographic techniques, the positioning of such locking screws or pins is typically the most time consuming and difficult portion of the overall rod implantation procedure.

Two other patents are thought to be of more general interest, U.S. Pat. No. 4,625,718 (Olerud et al.), and U.S. Pat. No. 4,570,624 (Wu). The Olerud et al. patent disclosing an aiming apparatus using X-ray techniques for making holes or bores in the bone of a patient in registration with the holes or bores on an interlocking nail, and the Wu patent disclosing a mechanical technique for aligning surgical pins in parallel.

Patents of interest in this field include U.S. Pat. No. 4,621,628 (Brudermann); U.S. Pat. No. 5,049,151 (Durham et al); and U.S. Pat. No. 5,514,145 (Durham et al). The Brudermann patent discloses an apparatus for locating transverse holes in the distal end of implanted locking nails. The apparatus includes at least one magnet which generates an axially symmetrical field, in combination with a magnetic field detecting device or sensor having an axial field reception characteristic. In one embodiment, the magnetic field sensor is inserted into an implanted nail and the magnet, which is placed on the surface of the skin, is moved until axes of the magnetic field of the magnet and the sensor are aligned. More particularly, the sensor is connected to an external display device and alignment of the respective magnetic fields is indicated when a zero-point indication is provided on the display device. A second magnet can be used to increase the precision of the alignment process. The directional characteristics of the magnetic field detection device are used to control the relative positions of the axes of both directional elements through a display device, such that both axes are brought into congruence with each other by means of the control display. When one of the directional elements is aligned exactly with the axis of the of the transverse hole in the in the nail, another element can be used externally to mark the location of the nail hole for positioning of a drilling jig.

The two patents by Durham et al. relate to a method and apparatus for positioning the screws or pins of orthopedic hardware devices such as intramedullary rods which involves the positioning of a first magnet at the location of a screw hole in the nail and then using an aiming device, comprising a second magnet which interacts with the first magnet, to locate the first magnet and hence enable a screw or pin to be placed in the screw hole in the nail to lock the nail in position.

In one first embodiment, an insertion rod is used to position the first magnet at the level of the hole in the rod while in another embodiment, a solid nail is used and the magnet is removable disposed within the hole in the nail prior to implantation of the nail.

One serious disadvantage common to the magnetic field detection devices is the detrimental influence of stray magnetic fields, such as, for example the earth magnetic field, or the effect of field distortion due to highly conductive materials in the form of aluminum, titanium, stainless steel and copper used in the construction of operating room tables and surgical implants. The art of using transmitting and receiving components with electromagnetic coupling for measuring position and orientation is well known especially with respect to armament sighting systems where the receiver component would be located in gunner's helmet and a transmitter component would be attached to a nearby electrically non-conductive structure. As the gunner would sight-in a target through a sighting cross-hair affixed to his helmet, the receiver located thereupon would pick up signals generated by the transmitter. These signals would then be processed by a computer to determine the position and orientation of the helmet and then to contemporaneously point a unit of armament in the same direction as the helmet mounted sight piece. As taught in U.S. Pat. No. 4,054,881 (Raab) and U.S. Pat. No. 4,287,809 (Egli et al.), and U.S. Pat. No. 4,314,251 (Raab) and U.S. Pat. No. 4,396,885 (Constant), an alternating current (AC) signal is applied in a time division or frequency division format to a transmitter consisting of two or three orthogonal coils which generate an AC electromagnetic field which is measured by an AC receiver likewise consisting of three or two orthogonal coils. These sensed signals are then filtered and amplified in a method compatible with the transmitted format, converted to a digital format and then read into a computer where various mathematical methods are resorted to in order to extract position and orientation with resort to applicable electromagnetic field equations.

All current systems such as the ones above, that utilize an AC transmitted signal work accurately only when there are no electrically conductive materials located near either the transmitter or receiver because any transmitted AC signal would invariably induce eddy currents in these conductive materials which would in turn serve to generate an AC magnetic field that would distort any transmitted field, and, of course, any ultimate out-put position and orientation data. In fighter aircraft or helicopters where it is desired to use these position and orientation measuring systems, there are a lot of highly conductive materials in the form of aluminum, titanium, magnesium, stainless steel, and copper used in the construction of the cockpit structure, seat, wiring and helmet-mounted displays. U.S. Pat. No. 4,287,809 teaches a method of compensating for the errors resulting from any field distortion due to cockpit metal that does not move with respect to the transmitter. The compensation method therein suggested involves making measurements throughout the cockpit to determine the amount of such distortion and then using this data to form a correction that is applied to the sensed signals. In a similar manner, U.S. Pat. No. 4,394,831 (Egli et al.) and U.S. Pat. No. 4,621,628 (Brudermann) teaches a method to accomplish compensation for errors due to eddy currents induced in metal such as would be found in a display located on a pilot's helmet or operating field, respectively. This compensation method again requires initial experimental measurements of such distortion in order to effect necessary corrections and provides moderate improvements in accuracy only when the amount of metal is concentrated in a single location and the transmitter does not go through large angular rotations or translations. These types of compensation efforts that are required to make AC systems work accurately are time consuming and expensive to perform and only work in environments where there would not be too much conductive material near transmitter or receiver units. In many locations, for example, AC systems cannot be utilized at all because the distortions produced are simply too large to be corrected merely by such mapping.

It is the object of this invention to provide an effective and economical device for the determination of the location and orientation of the holes in orthopaedic implants. Still another object of the present invention is to provide a targeting device which can be utilized by the majority of current intramedullary nails currently available to the surgeon.

SUMMARY OF THE INVENTION

The invention includes a two- or three-axis transmitter positioner driven by a pulsed DC current, external to the patient, coupled with three- or two-axis receivers positioned internal and/or external to the implant. The receivers are sensitive to a transmitted DC magnetic field emanating from the activated transmitter. Receiver signal processing electronics control the receiver and serve to convert its output to a format suitable for processing by a digital computer in conjunction with a method for processing received signals so as to thereby develop position and orientation data of the transverse locking holes or pin placement. Such data then can be graphically displayed to the user so as to guide the user for accurate alignment of a drill bit with the transverse holes in the implanted device.

The devices presented in U.S. Pat. Nos. 4,945,305 and 4,849,692 (Blood) represents a radical departure from all of the prior art relating to such transmitting and receiving position and orientation devices, insomuch as it avoids, in-toto, resort to AC signals and instead relies upon direct current (DC) signals. Such reliance on DC signals obviates completely any need for a prior calibration undertakings and greatly expands the potential utility of devices of this type. Moreover, manufacture and utilization of this device for purposes of accomplishing all that current devices can accomplish is manifestly less expensive than such manufacture and utilization of said currently used devices are or potentially will be.

It has now been found that the use of the devices of U.S. Pat. Nos. 4,945,305 and 4,849,692, the disclosure of which are incorporated by reference herein, as though recited infull, can be applied to the installation of orthopaedic implants and, more particularly, to the locating of holes in an implanted prosthesis so that a screw or pin for interlocking the prosthesis either with itself or with the surrounding bone can be accurately installed, with surprising effective results.

The invention provides a system of transmitting and receiving antennae that by themselves intrinsically and with inherent electronic means together with a digital computer readily measure position and orientation relative to one another without the need for expensive calibration procedures undertaken in advance of implementation and further without concern for what types of diamagnetic or paramagnetic metallic materials such as may be nearby. For the first time, for instance, devices of this nature can be used in surgical procedures in conjunction with metallic implants and surgical apparatus.

The invention provides for the determination of the displacement vector and determination of the orientation of the orthogonal axis of the receiver relative to the transmitter, FIG. 1. The transmitter is considered the origin of an orthogonal coordinate system of x, y, and z coordinates wherein the z-axis is considered, generally, in line with the gravitational axis of the earth, the x and y axes then lie in the horizontal plane, perpendicular to the z axis and according to a Cartesian coordinate system. The Cartesian system consists of three mutually perpendicular lines or axes that intersect at a common point such that the location of a point relative to the origin can be determined without ambiguity. In addition, each receiver establishes a reference coordinate system with respect to the respective receiver and relative to the transmitter origin such that the location of the receiver can be determined from the transmitter, as well as the rotation of each axis of the receiver system relative to the transmitter. It is an advantage of the invention that the coordinate reference system of the receiver can be electronically offset to a desired location using the inherent electronic means together with a digital computer. As shown in FIG. 6, the reference axis S1 of receiver 107 at location r1 can be electronically offset to a location r1' with a reference axis S1' such that the location vector and the angular orientation of the axis S1' from the transmitter can be ascertained. Likewise, the receiver axis of each receiver can be offset to any desired positioned.

It is a further advantage of the invention that the relative position and orientation between two or more offset locations can be ascertained using the inherent electronic means together with a digital computer. It is a further advantage that the relative distance between two or more offset axes can be minimized such that one or more of the relative components of the relative displacement vector be minimized and the corresponding axes aligned in space.

The invention provides a distinctly less expensive sighting device than is currently provided within the framework of the present state of the art separate and apart from the cost savings to be realized from abrogation of calibration requirements. Presently, the cores of the transmitting components of these devices are made up of Ferrite. Ferrite is rather expensive, but, in addition to this, it is also rather fragile and difficult to shape. However, Ferrite is necessary as a core piece in order to keep eddy current distortion acceptably low where AC current is used. But, there are no AC signal components in the instant device's steady state signal and hence, the same magnetic flux concentration as can be had with Ferrite can likewise be had and used with this device by resorting to less expensive iron or steel for a transmitting core piece, since, with this device, there is no need to be concerned with eddy currents at all.

The instant invention provides a targeting apparatus which does not require the use of radiographic radiation in determining the location of the transverse holes of intramedullary implants, particularly of the distal holes of interlocking nail. The apparatus of the present invention provides, fast, convenient and secure placement of the drilling jig in axial alignment with the transverse holes without involving the radiation exposure on the surgeon, patient, and other medical personnel. The current surgical practice in the use of the image intensifier to locate the unseen transverse holes in the implant and to target the hole for drilling and placement of interlocking screws exposes the surgeon to excessive amounts of radiation during the course of the procedure.

Another advantage of the present invention is that it provides a targeting device which can be utilized by the majority of current intramedullary nails currently available to the surgeon. The current mechanical locating devices are usually implant specific and require the use of the image intensifier to locate the orientation of the distal locking holes. The Distal Targeting Device described in the Russell-Taylor Surgical Technique brochure (Smith & Nephew Richards, Memphis Tenn.) is a "bombsite" apparatus which is mechanically fastened to the proximal end of the nail and utilizes the image intensifier to locate and drill the necessary holes. The mechanical targeting system described in U.S. Pat. No. 4,913,137 is specific to that device. The targeting mechanism described by Azer et al requires that the described nail have a bifurcated tip, a cross section complimentary to other instrumentation, and a mechanism for attachment to the proximal end of the nail. The rod mounted targeting mechanism described in the surgical technique for the Alta Trauma System by Howmedica (Rutherford, N.J.) requires the initial location of the distal holes, the attachment of the targeting assembly mechanism to the nail, and further fluoroscopic control to position the targeting assembly over the distal holes. Another technique used for the above systems, as well as all the other nail systems, requires the use of direct fluoroscopic imaging to locate and align the holes with out any mechanical or electrical connections is called "free handing". This technique is described in detail in the brochures by Smith & Nephew Richards, Zimmer (Warsaw, Ind.), Ace Medical (Los Angeles, Calif.) and Biomet (Warsaw, Ind.).

The described technique and devices of the present invention can be customized for any of the described intramedullary nails.

In accordance with the invention, a DC coupled electromagnetic sensor is provided which is easier to use than prior art devices and which provides easier and more accurate alignment than is afforded by the prior art. In this regard, although the positioner arrangement of the Brudermann and Durham et al. patents discussed above possesses a number of important advantages over the radiographic locator devices, the present invention provides important additional advantages over the positioner arrangement disclosed in those patents, particularly in the areas of ease of use and ease and quality of the alignment.

In one aspect of the invention, a DC coupled electromagnetic positioning system is provided for assisting in positioning a fastening element at a desired concealed internal location such as at a locking screw hole in an intramedullary rod in the bone of a patient, the arrangement comprising: a pulsed DC current transmitter, a first receiver, or a plurality of receivers, that is sensitive to the transmitted DC magnetic field adapted to be positioned at said internal location and providing a two or three axis directional reference or coupled with the implant at a known offset location and orientation from the internal location to be positioned; and a second or additional receivers thus providing multiple reference positioning devices external to the patient; the positioning device comprising a hand-held drilling jig or guide drill having an axial bore there through, so as to enable the external receiver to align with the internal or couple receiver, the positioning device further comprising a guide pin insertable into the axial bore and adapted to be engaged by the drill chuck of said drill when the perceived axes of the first and second receivers are aligned so as to enable the guide pin to be advanced by the drill along a path of travel in alignment with the internal location.

In an advantageous embodiment, the said first receiver or internal sensor unit is embedded in a unit or handle to which the implanted device is attached. The location and orientation of the receiver relative to each internal concealed location to be positioned can be known through either physical measurement or electronic determination using a calibration routine. In an advantageous embodiment, the said first receiver or internal unit includes a protective cover. Preferably, the protective cover comprises a plastic casing advantageously shaped to match or conform to the internal shape of the particular intramedullary device being implanted. Thus the embodiment of the invention involves the provision of a locating arrangement that can be used with any commercial nail.

In an advantageous embodiment, the perceived position of the first and second receiver, or additional receivers, relative to the transmitter, can be electronically offset by the connected computer so as to provide a perceived location and axis in space, relative to the sensors. The advantage of this embodiment is that the position and axis of the transverse holes can be ascertained without the sensor being physically at the location. With both the first and second sensors offset to the same position, an axis and location of the transverse hole can be located and a drill or pin passed through the hole without interference from the sensor.

BRIEF DESCRIPTION OF THE DRAWINGS

FIG. 5 illustrates the drill guide and drill sleeves

DESCRIPTION OF THE PREFERRED EMBODIMENTS OF THE INVENTION

Figure 1:
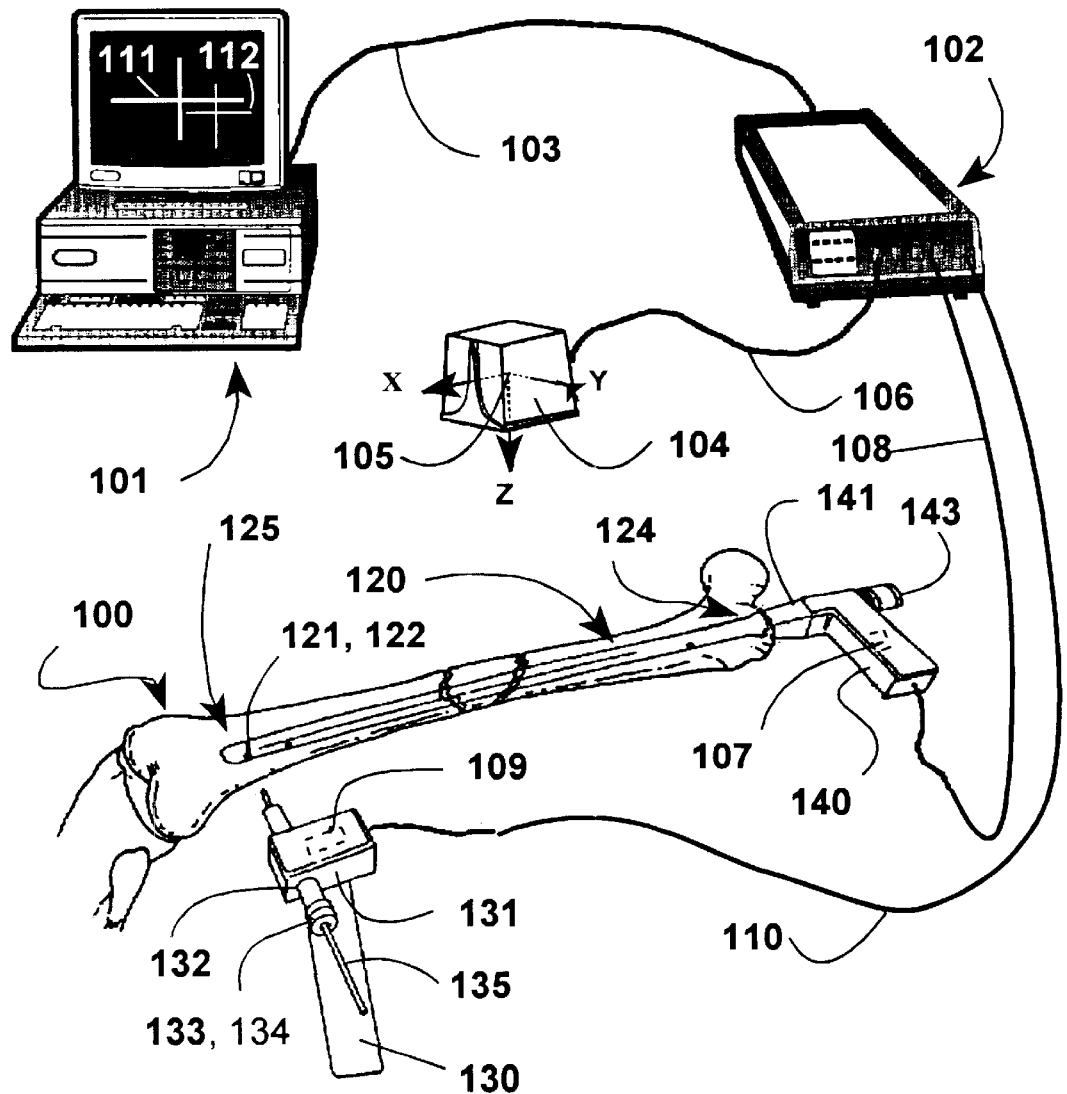
FIG. 1 illustrates the components of the invention and positioning of an interlocking nail 120 in the medullary canal of a bone 110.

A first component, such as an orthopaedic implant, and more particularly an intramedullary nail is provided with at least one connector receiving mechanism. In the case of an intramedullary nail, the connector can be a screw and the connector receiving mechanism can be holes in the nail. A drill guide member, is used to guide a drill bit towards a selected hole in the nail. The drill bit is positioned and oriented by the drill guide member relative to the intramedullar nail. The guiding system includes:

(a) a direct current magnetic field transmitting member;

(b) at least one magnetic field receiving means for receiving the transmitted direct current magnetic fields;

(c) power means for supplying direct current electrical signals to the transmitting means for creating the transmitted direct current magnetic fields;

(d) receiver electronics for measuring, and converting out-put signals from the magnetic field receiver electronics, into position and orientation measurements; and (e) programmed computer, the programmed computer having a visual display member, the output signals from the receiver electronics being converted into position and orientation measurements and visually displayed on the computer visual display member.

The first component is fixed to either the transmitting member or the receiving means. Similarly, the drill guide member is fixed to either a transmitting member or a receiving means.

Preferably, the system employees a single transmitter, and both the drill bit guide member and the intramedullary nail are provided with receivers. Thus, the relative position and orientation of the first member relative to the drill guide member can be determined. The intramedullary nail has a proximal end and a distal end. A support member, such as a handle, is releasably secured to the proximal end of the nail and carries a receiver. The transmitter for transmitting direct current magnetic fields comprises a core and a multiplicity of roughly orthogonal antenna axis wire windings. The receiver of the transmitted direct current magnetic fields comprises a multiplicity of roughly orthogonal antennae axes that are sensitive to transmitted direct current magnetic fields.

The method of securing an implant, such as an intramedullary nail into a bone includes the steps of inserting the implant into a bone, drilling a hole in the bone proximate the screw receiving hole in the nail, by using a drill member and a drill guide. The determination of the position and orientation of the drill member relative to the holes involves (a) transmitting a direct current magnetic field from a transmitting member, receiving the transmitted direct current magnetic fields at at least one magnetic field receiver. The nail is fixed to either the transmitting member or the receiving means, preferably, the receiver. Similarly the drill guide is fixed to either a transmitting member or the receiving means, preferably, the receiver. The received direct current magnetic fields are converted into position and orientation data in a programmed computer, and displayed on the computer screen. By viewing a virtual representation of the nail and the drill member on the computer screen, the drill member can be moved to the desired location relative to the intramedullary nail.

Advantageously, the nail receiver can be remote from the screw receiving hole so that the receiver need not be carried into the bone along with the nail. The computer program calculates the offset from the receiver to the hole, and thus, the display shows the position of the hole relative to the drill.

Figure 3A:
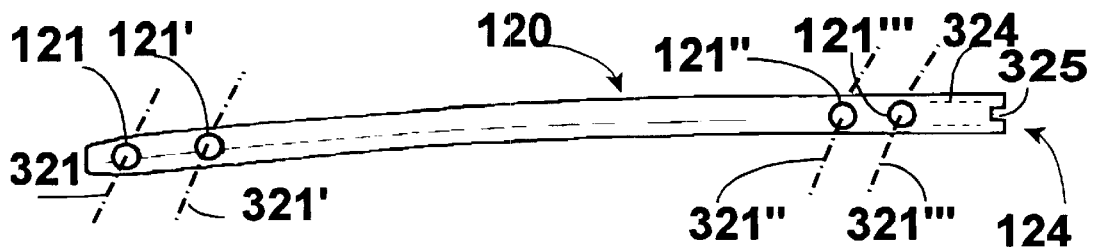
FIG. 3 illustrates the intramedullary nail
Figure 3B:
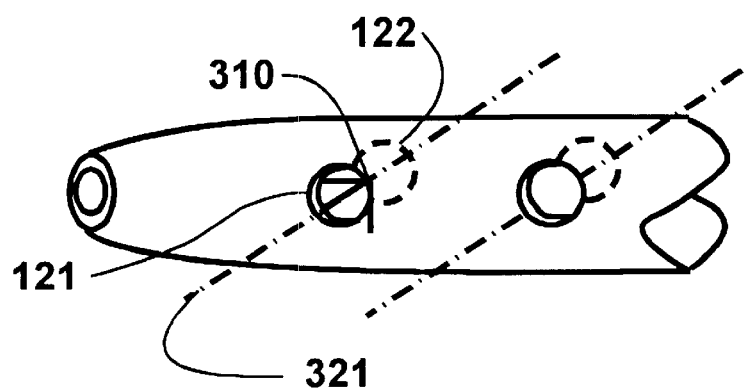
Figure 3C:
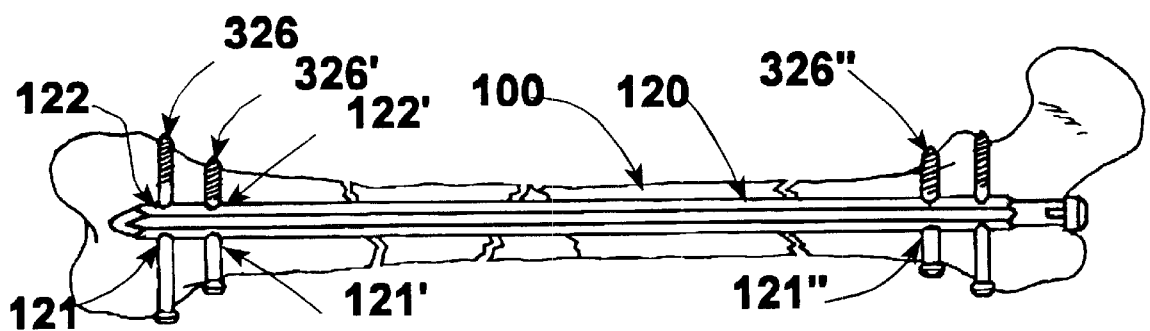

In FIG. 1, the nail 120 has been driven into the bone 100 from the right side, and the nail has in the vicinity of its left, i.e. distal end 125 a pair of transverse holes 121 and 121 and in the vicinity of its right, i.e. proximal, end a transverse or oblique hole 121" for receiving transverse bolts 326, 326, and 326", FIG. 3, respectively.

Next, the exact position of the respective drilling axis 321 of a most distal hole 121 in the intramedullary nail 120 is to be determined. This drilling axis can be definitely determined by a linear connecting line of the two center points 322 and 323 on this axis. In order to place a drilling jig 131 in a position aligned with this axis, the two points 322 and 323 on the drilling axis of the distal hole 121 must be located accordingly, and the axis of the drilling jig 532 must be oriented in accordance with these points, whereupon the hole (bore) may be formed in the bone immediately.

The apparatus according to the invention is used for locating the axis 321 generated by these two center points 322 and 323. The electromagnetic position and orientation measuring system, as described in U.S. Pat. Nos. 4,945,305 and 4,849,692, consisting of: a transmitter driver circuit within an electronic control unit 102 for providing a controlled amount of DC current to each of two or three axes of transmitter 104 one at a time. The amount of DC current provided by driver 102 to the transmitter to the signal processing electronics, via connection 106, is controlled by the computer 101. The transmitter 104 is usually located within a few feet of distance from a patient's leg.

Figure 2:
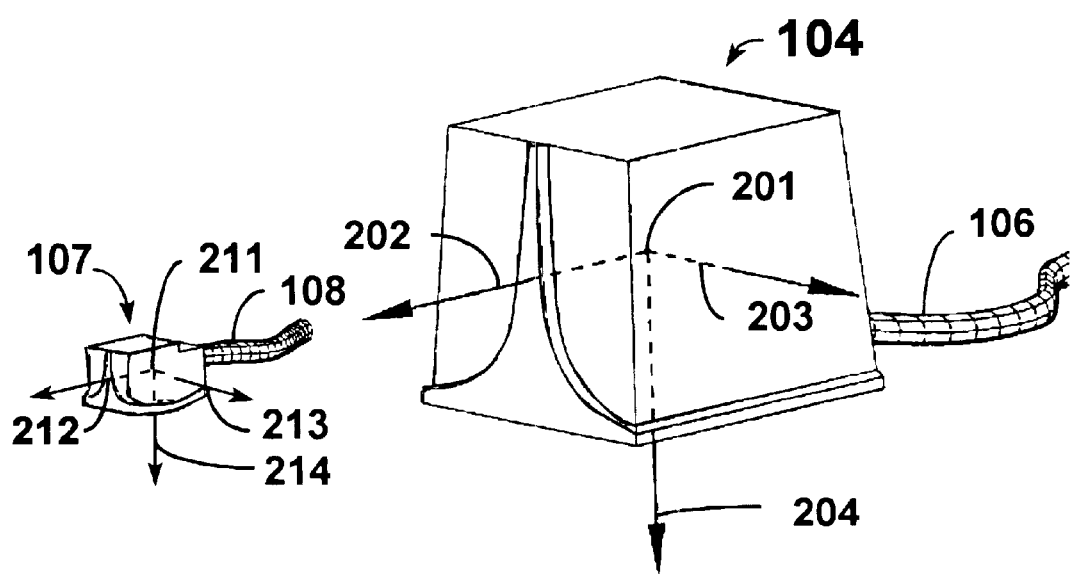
FIG. 2 illustrates the coordinate axis for the transmitter 104 and receiver 107.

In FIG. 2, transmitter 104 consists of three individual antennae 105 (x 202, y 203, and z 204 axis, FIG. 2) arranged concentrically which generate a multiplicity of DC magnetic fields that are picked up by receiver 107 and receiver 109, (FIG. 1) of the receivers 107 and 109 are also each composed of three antennae (x 212, y 213, and z 214 axis antennae). Receivers 107 and 109 measure not only the fields generated by transmitter 104 but also the earth's magnetic field to thereby effect an ultimate measurement of the position and orientation of the object to which it is attached. The transmitter antennae represent a Cartesian coordinate system 105 with an origin 201 located at the center of transmitter 104 and having three orthogonal axes; an X axis 202, a Y axis 203 and a Z axis 204. Likewise, each receiver 107 and 109 have receiving antennae which represent a Cartesian coordinate system 210 and 220, respectively. The coordinate system 210 of receiver 107 has an origin 211 located at the center of receiver 107 and having three orthogonal axes; an X axis 212, a Y axis 213, and a Z axis 214. Not shown in FIG. 2, but numbered accordingly, the coordinate system 220 of receiver 109 has an origin 220 located at the center of receiver 109 and having three orthogonal axes; an X axis 222, a Y axis 223, and a Z axis 224.

Receiver 107 and 109 consists of three or two axes, 210, 220, respectively, with driving and detecting circuits that are sensitive to DC magnetic fields. The DC signal output from receiver 107 goes to the signal processing electronics 102 via connection 108. Signal processing electronics 102 controls, conditions, and converts analog receiver signals into a digital format that can be read by computer 101. Computer 101, by way of an algorithm, computes the position and orientation of receiver 107 and 109 with respect to transmitter 104. Computer 101 then outputs this information to a graphic image controller by which the surgeon can view the relative position of the guide 131 with respect to the nail driver 140 and thus to the axis 321 of hole 121 of FIG. 3A.

Figure 4:
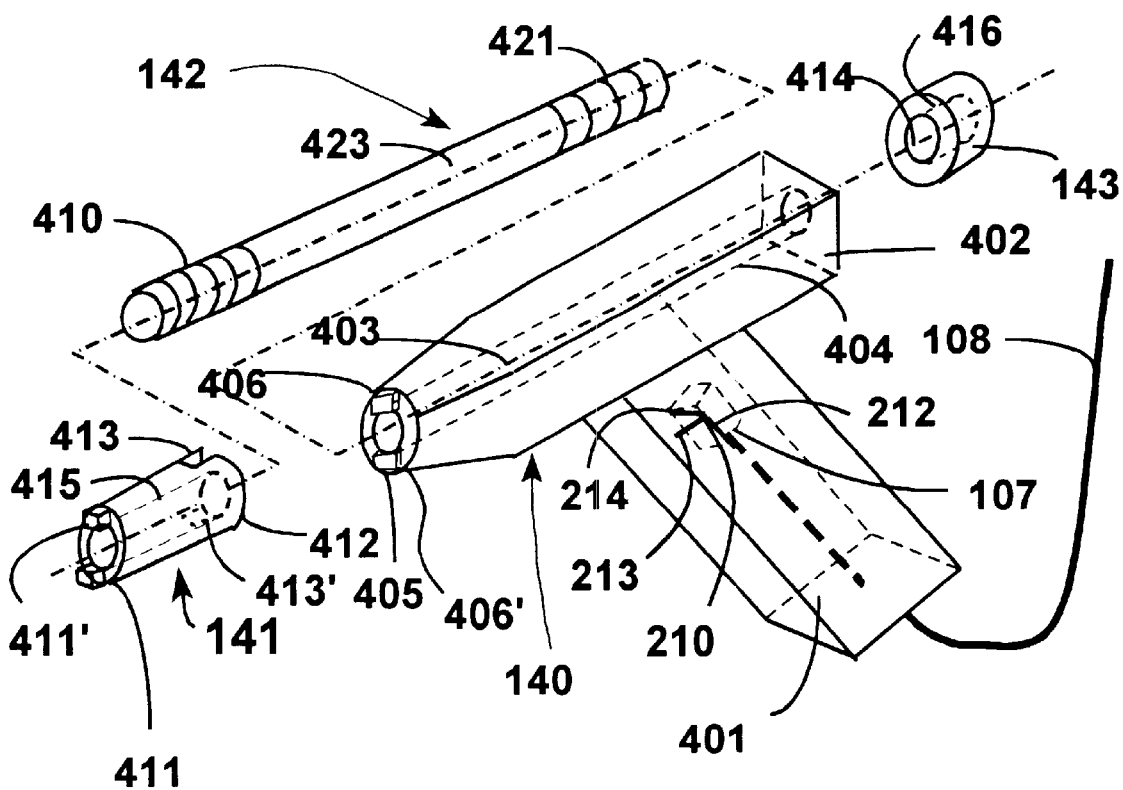
FIG. 4 illustrates the nail driver and associated components

As illustrated in FIG. 4, the receiver 107 is mounted on, or is embedded in, a driver unit 140 used to implant the nail 120 in the bone 100. The nail driver 140 is comprised of a handle 401 and longitudinal body 402. The longitudinal body 402 has a longitudinal cylindrical bore 404 with central axis 403 which is coincident with the longitudinal axis of the intramedullary nail when attached securely to the nail using the specific nail attachment 141 and connecting bolt 142 and locking nut 143.

Nail attachment 141 has an indentation or similar means to align with the protrusion 406 and 406' or other mechanism on end 405 of the longitudinal body 402. Nail attachment 141 has a central bore 415 extending the longitudinal axis of the attachment coincident with the central axis 403. The nail attachment has protrusions 411, on the end opposite from the end having indentations 413, 413' to provide alignment of the attachment with the indentations 325 located on the proximal end 124 of intramedullary nail 120 as shown in FIG. 3A.

A connecting bolt 142 comprised of threaded end 410, body 423, and threaded end 421 is used to fasten and align the nail 120 with the nail driver 140. Bolt end 410 is formed to mate with the threads 324 on the proximal end 124 of the nail 120. The attachment spacer 141 is slid over the bolt 142 by placing the bolt 142 through the central bore 415. The nail driver 140 is likewise slid over the bolt by placing the bolt through the cylindrical bore 404 of nail driver body 402 such that the protrusions 406 and 406' interlock with indentations 413 and 413', respectively. With the spacer 141 engaged with the nail 120 and nail driver 140 engaged with the spacer 141, the locking nut 143 is threaded on threads 421 of the connecting bolt 142.

Figure 5A:
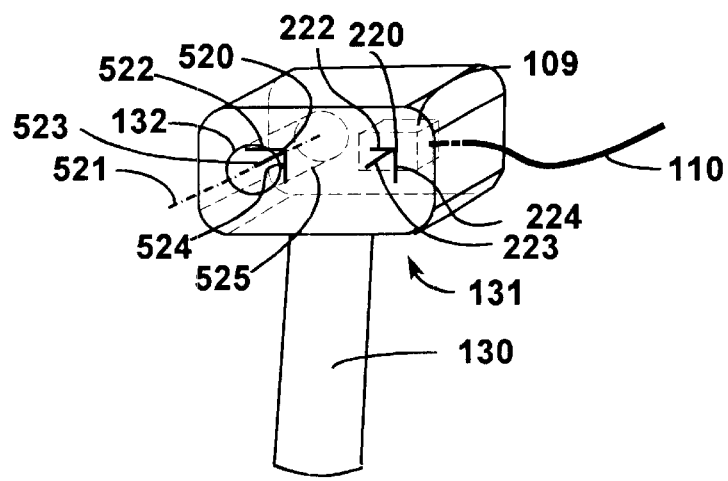
FIG. 5A illustrates the drill guide and drill sleeves
Figure 5B:
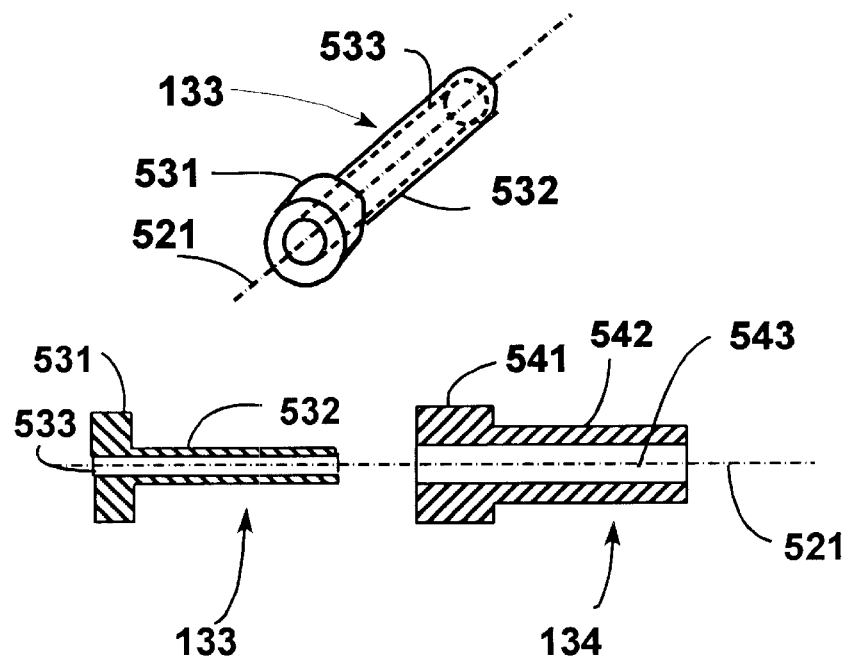
FIG. 5B is an exploded view of the drill sleeves for use with the drill guide of FIG. 5A

Receiver 109 is preferably attached to, or embedded in a hand-held guide 131 of FIGS. 5A and 5B. Guide 131 is constructed to receive an outer sleeve 134 within the drill guide hole 132. Inner sleeve bore 525 has an entrance 132 and a central axis 532. Drill sleeve 133, has a central bore 533 enabling drill bit 135 to be coincident with the longitudinal axis 532 when drill sleeve 134 is inserted in bore 525.

The controlling computer 101, by way of an algorithm, is able to electronically transpose, both in translation and rotation, the axis 220 and x 222, y 223 and z 224 to a new location 520 such that the offset coordinate axis can be located on the longitudinal axis 532 or the central bore 533. The computer then computes the position and orientation of the offset axis 520 with respect to transmitter 104. Computer 101 then outputs this information to a graphic image controller by which the surgeon can view the relative position of the drill guide axis 532, as viewed as cross-hairs 112 in FIG. 1, with respect to the nail driver 140, as viewed as cross haris 111, in FIG. 1, and thus to the axis 321 of hole 121.

Likewise the computer 101 by way of an algorithm, is able to electronically transpose, both in translation and rotation, the nail driver's receiver axis 210 to a new location 310 such that the offset coordinate axis can be located on the axis 321 of hole 121. The computer then computes the position and orientation of the offset axis 310 with respect to transmitter 104. Computer 101 then outputs this information to a graphic image controller by which the surgeon can view the relative position of the drill guide axis 532 (cross haris 112) with respect to this offset axis 310 and thus to the axis 321 of hole 121 (cross hairs 111).

Figure 6:
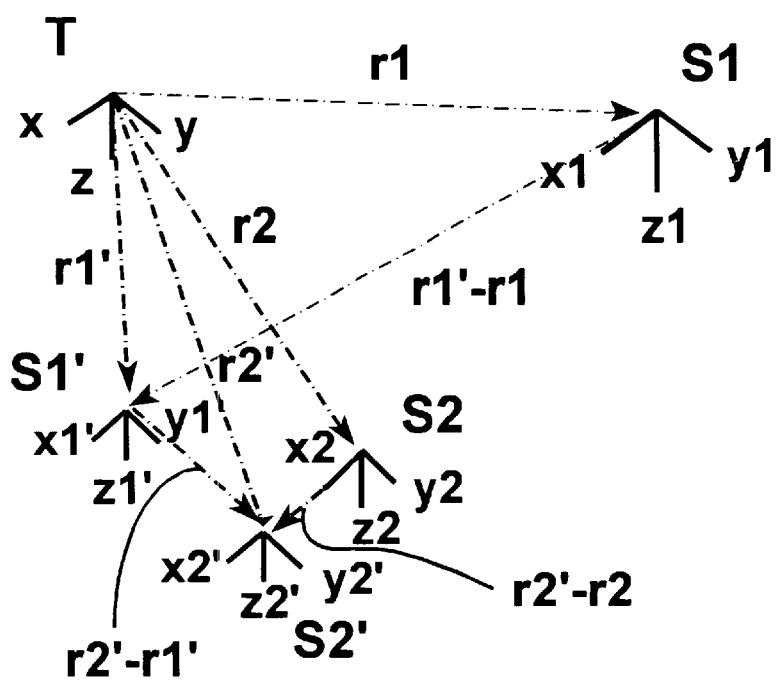
FIG. 6 illustrates the displacement vectors of the receiver 107 and receiver 109 and axis offset positions to the transverse hole 121 and axis of drill guide bole 132, respectively, relative to transmitter coordinate origin 201.

The mathematical relationship for the distance from the offset axis of the transverse hole 310 to the offset axis 520 of the drill guide 131 can be derived from the position vectors (small letters in bold). FIG. 6 presents a schematic of the position vectors of the system. T is the location of transmitter axis 104 (0,0,0) from which the positions, r1 to the axis S1 210 (x1, y1, z1) of the sensor 107 embedded in the nail holder 140, and r2 to the axis, S2 220, of the sensor 109 embedded in the drill guide 131 are measured electronically by the computer 101 and electronic control unit 102. Likewise the orientation of the offset axes, S1' 310 and S2' 520, are determined relative to the sensor axes, S1 210 and S2 220. The transverse hole to be drilled has an axis S1' 310 which is physically positioned, r1'–r1 from S1 210. This offset position vector, r1'–r1, is determined at the time of surgery, prior to implantation, as part of the calibration procedure. This value will be dependent upon the length of the nail chosen as well as the orientation of the transverse hole. The drill guide hole in the drill guide has an axis S2' 520 which is offset from sensor axis S2 220 by a distance r2'–r2. The offset position vector, r2'–r2 is a constant which is determined from the manufacturing of the drill guide unit 131 and stored in the software. Therefore knowing the above vectors, the vector, r2'–r1' can be determined from the vector relationships:

$$(r2'-r1')=r2-r1+(r2'-r2)-(r1'-r1)$$

The software algorithm stored in the computer 101 will provide the relative distance and orientation of the offset holder axis to the nail's transverse hole which in turn can be viewed on the computer monitor by the user.

Procedure for Using the Device

The distance and orientation, as depicted by the vector (r2'–r2, FIG. 6) of the axis of the drill guide hole 532 relative to the drill guide sensor 109 are constant and known. However, the distance from the receiver 107 in the driver to the axis 321 of the intended hole 121 will be dependent upon the length of the intended implant 120 as chosen be the surgeon. Thus prior to insertion, the distance and orientation of the transverse hole(s) 121 relative to the holder receiver 107 must be determined. This can be performed in a simple "calibration" procedure.

Figure 7:
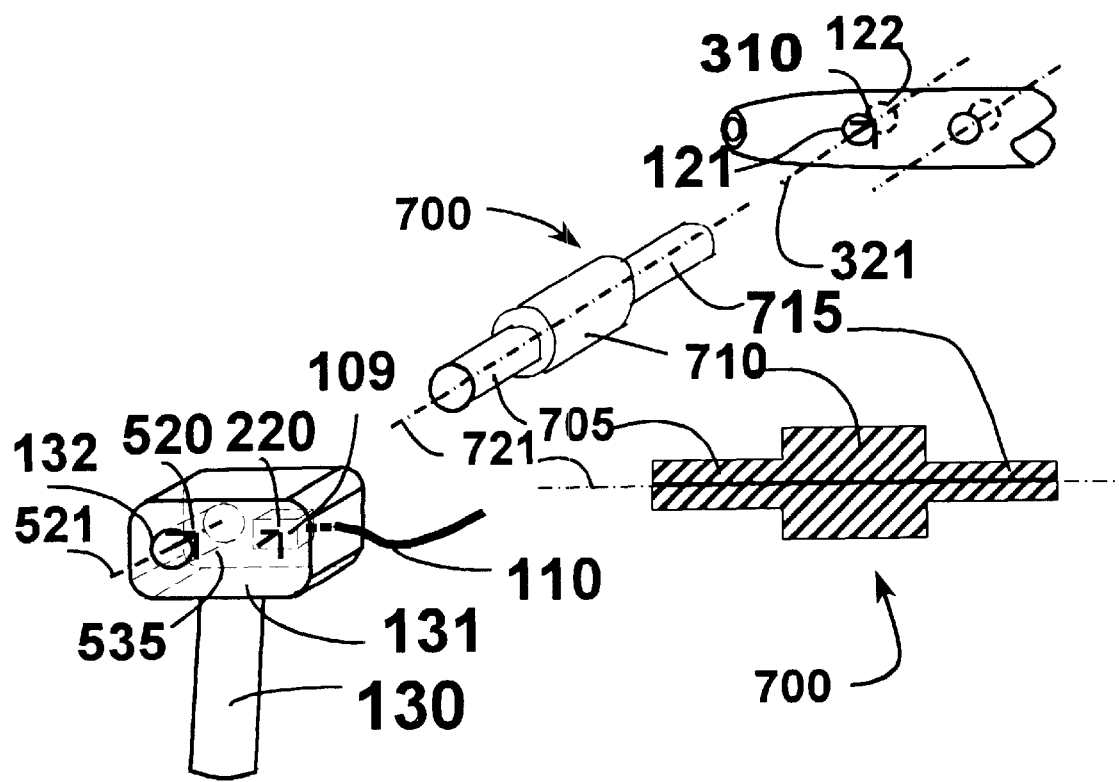
FIG. 7 illustrates the calibration tool used with the grill guide and intramedullary nail.

The computer 101 determines the position of the receiver 107 relative to the transmitter 104, but it is desirable to know the position of the axis 321 of the transverse hole 121 relative to the holder sensor. A "calibration" must be performed to determine the offset distance, vector r1'–r1, from the holder receiver 107 to the axis 321 of the transverse hole 121. An alignment pin 700, as illustrated in FIG. 7, is composed of an initial cylindrical segment 705 which is of such diameter or complimentary shape as to fit into bore 525 or bores 533 or 543 of the drill sleeve 133 or 134, respectively, a central section 710, and a third section 715 which is of such diameter or complimentary shape as to fit into holes 121 and 122, is placed in the drill guide hole 525 and inserted in the first of the nail's transverse holes 121. Thus the alignment pin 700 longitudinal axis 721 causes the axis of 521 to be coincident with axis 321. Thus the location of the distal hole axis 520, S1' is now known relative to the drill guide receiver axis 210, S2, and thus to the transmitter 104 and the nail driver receive 107, S1. With the alignment pin 701 in place, the location and axis of the transverse hole 321 relative to the nail driver receiver 107 is computed using an algorithm and digitally stored by the computer 101. The alignment pin 700 and drill guide is moved to the second transverse hole 121' and it's location and axis 321' relative to the nail driver 140 is likewise computed and stored in the computer 101. The procedure is repeated for any additional locking holes in the nail such that the computer has stored the location and axis of each transverse locking hole relative to the handle sensor. Thus the relative distance and orientation of each transverse hole, relative to the sensor in the nail driver is known and the computer has digitally stored the offset coordinates of each hole in the nail for finding the hole after the nail has been implanted.

After the hole locations are stored in the computer 101, the nail 120 is inserted into the bone 100. The computer program then prompts the surgeon to place the drill guide 131 at the first hole location 121. A stationary three dimensional cross-hair 111, representing the position of the axis 321 of the desired transverse hole 121 is displayed on the computer monitor. A second three dimensional cross hair 112 is displayed on the monitor which represents the location and orientation of the drill guide axis 321 relative to the offset axis 310 of the desired transverse hole 121. The surgeon then moves the drill jig until the guide's cross hairs 112 are aligned with the stationary cross hairs 111 on the monitor. The axis of the drill guide 532 is now aligned with the axis 321 of the transverse hole of the nail. The drill guide is held firmly in this orientation or gently taped to set it in the bone 100, a drill 134 is inserted in the drill sleeve 133 and drilled through the nail hole 121. The drill 134 is removed and a screw 326 inserted to lock the nail with the bone. The computer is then programmed to proceed to the second hole 121' and the procedure repeated. The procedure is repeated until all the holes have been locked.

Figure 8A:
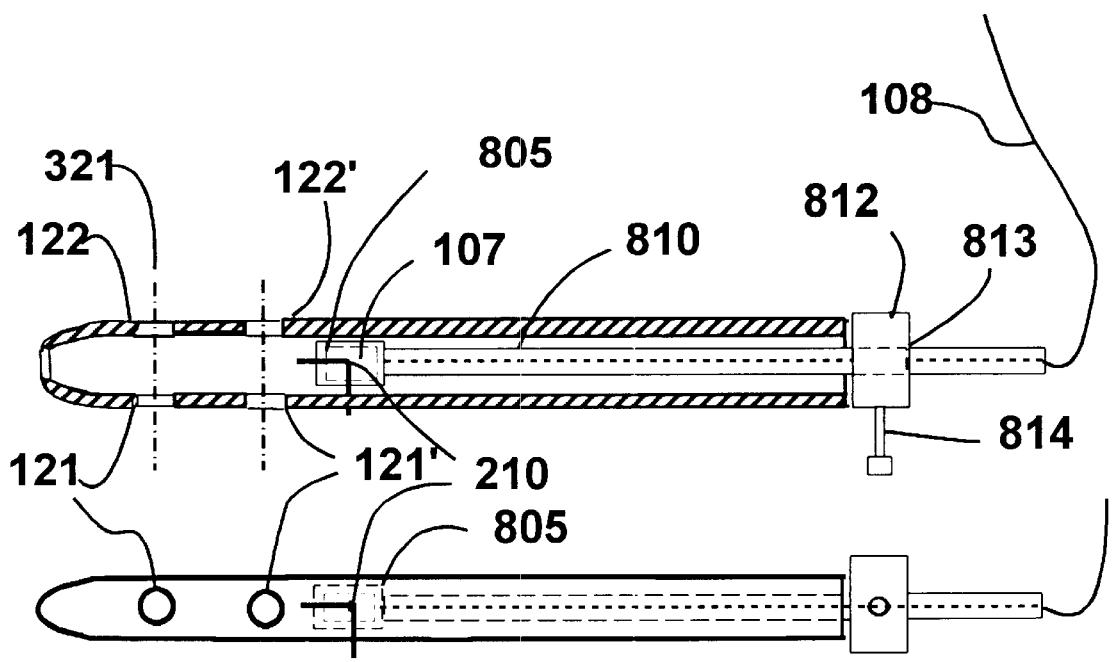
FIG. 8a illustrates the application of the invention with the receiver positioned within a probe inserted in the intramedullary nail.
Figure 8B:
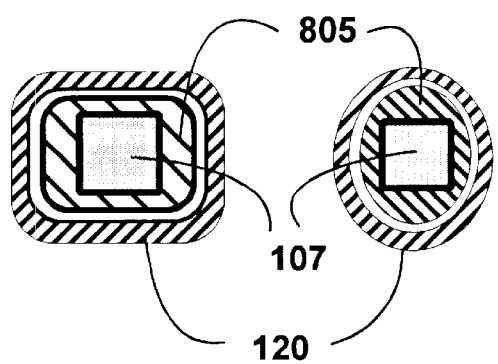
FIG. 8b illustrates the cross section of different shaped probe heads complimentary to the intended implant 120.

In a further embodiment of the invention, as illustrated in FIG. 8, receiver 107 is be embedded within a probe head 805, connected to probe 810. The electrical connection for receiver 107 would be contained within probe 810 and connect to the signal processing unit 102 via wire 108. Correspondingly differently shaped probe heads 805 are required for different nail diameters or different profile (cross-sectional) shapes of the nail, FIG. 8b, respectively, to ensure that during insertion of the probe head 805 that the probe head 805 does not rotate relative to the nail 120 such that the orthogonal axes 210 of the receiver 107 remains along the orthogonal axes of the nail 120.

The exact orientation of the receiver 107 at the distal end of the probe head 805 in the longitudinal direction of the nail 120 relative to the axis of the transverse hole 321 is obtained by the fact that the spacing of the transverse hole 121 from the proximal end 124 of the nail 120, with a realistically pronounced deformation and in consideration of the elastic deformability of the probe 810 in the shank thereof, is maintained with a sufficient degree of accuracy. For varying lengths of nails or for the various distal holes 121 or 121' of the nail 120, a stop member 812 needs be positioned and fixed on the probe shank 810 in correspondingly different positions prior to inserting the probe head 805 into the nail 120. The probe shank 810 would have gradation markings corresponding to the distance from the proximal end of nail 120 to the hole axis 121 minus a specified setback distance to place the probe head 805 and receiver 107 proximal to the hole 121 to ensure that the probe head 805 is not compromised during the drilling procedure.

The DC signal output from receiver 107 goes to the signal processing electronics 102 via wire 108 which controls, conditions, and converts analog receiver signals into a digital format that can be read by computer 101. Computer 101, by way of an algorithm, computes the position and orientation of receiver 107 with respect to transmitter 104, the position and orientation of receiver 109.

The position of the drill guide 131 relative to the transmitter 104 is likewise computed using the DC signal output from receiver 109 via connection 110 the signal processing electronics 104 and displayed on the computer's 101 display device. The distance and orientation of the axis of the guide receiver 109 relative to the axis 532 of the hole in the drill guide 131 will be equal to predetermined set back distance of the origin of the axis 210 of the probe head receiver 107 from the hole axis 121 or 121'. Therefore relative position of the axis of the drill guide 532 with respect to the axis of the nail hole 121 can be visualized and aligned with the axis 321. Upon alignment of the axes, a drill is passed through the bone 100 and nail hole 121 and withdrawn. A screw or locking bolt 326 is inserted in through the drilled hole and nail.

After performing the above operations at the most distal hole 121, a second bolt 326' is placed into the corresponding hole (bore) 121' using the same procedure.

After performing the above operations at the distal end, the proximal bolt 326" is to be placed into the corresponding hole (bore) 121", and this operation need not be described in greater detail here since, owing to the small distance to the proximal end of the spike, a conventional location and drilling device as described in the referenced patents may be used with a sufficient degree of precision for the locating of the proximal holes.

Figure 9A:
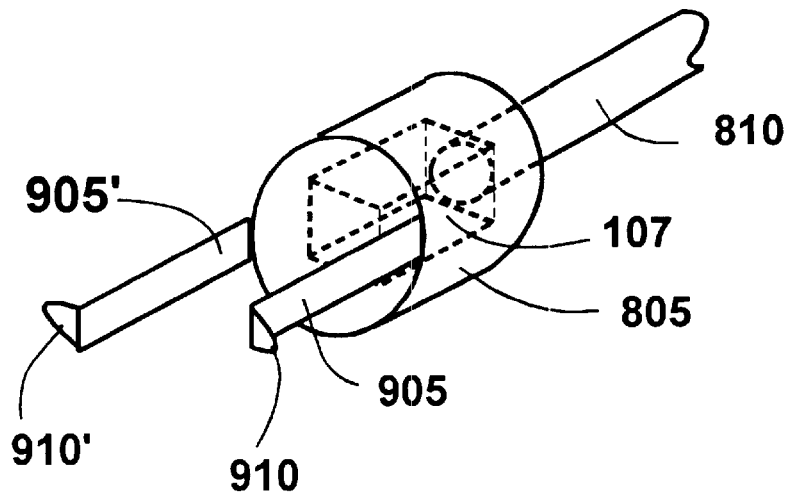
FIG. 9A is a perspective view that illustrates the components of the probe when used with a circular cross section implant.
Figure 9B:
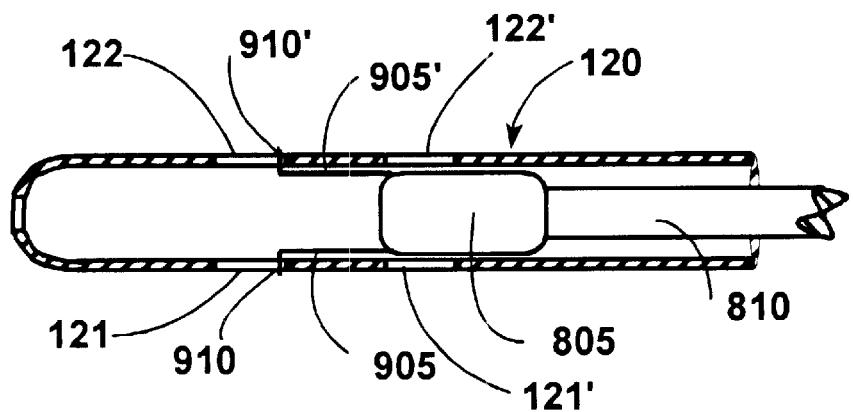
FIG. 9B is a side view of the probe of FIG. 9A.

It should be noted further that the apparatus is capable of operating effectively even if the probe head cannot be guided by the inner profile of the implant, such as, for example, in the case of nails having a circular cross-section. In such instance, auxiliary measures may be taken in order to align or orient the probe head relative to the transverse hole. For example, this may be effected with the aid of a holding device adapted to engage into the hole. FIGS. 9A and 9B show a method by which the probe head 805 has finger extensions 905 and 905' with prongs 910 and 910', respectively, and such prongs are able to engage the near edge of holes 121 and 122, respectively, thus provide a rotational and longitudinal position of the probe relative to the hole. The length of the probe extension in addition to the radius of the hole can be made equal to the distance from the axis of receiver 109 and the axis 521 of the drill guide bore 535.

Figure 10:
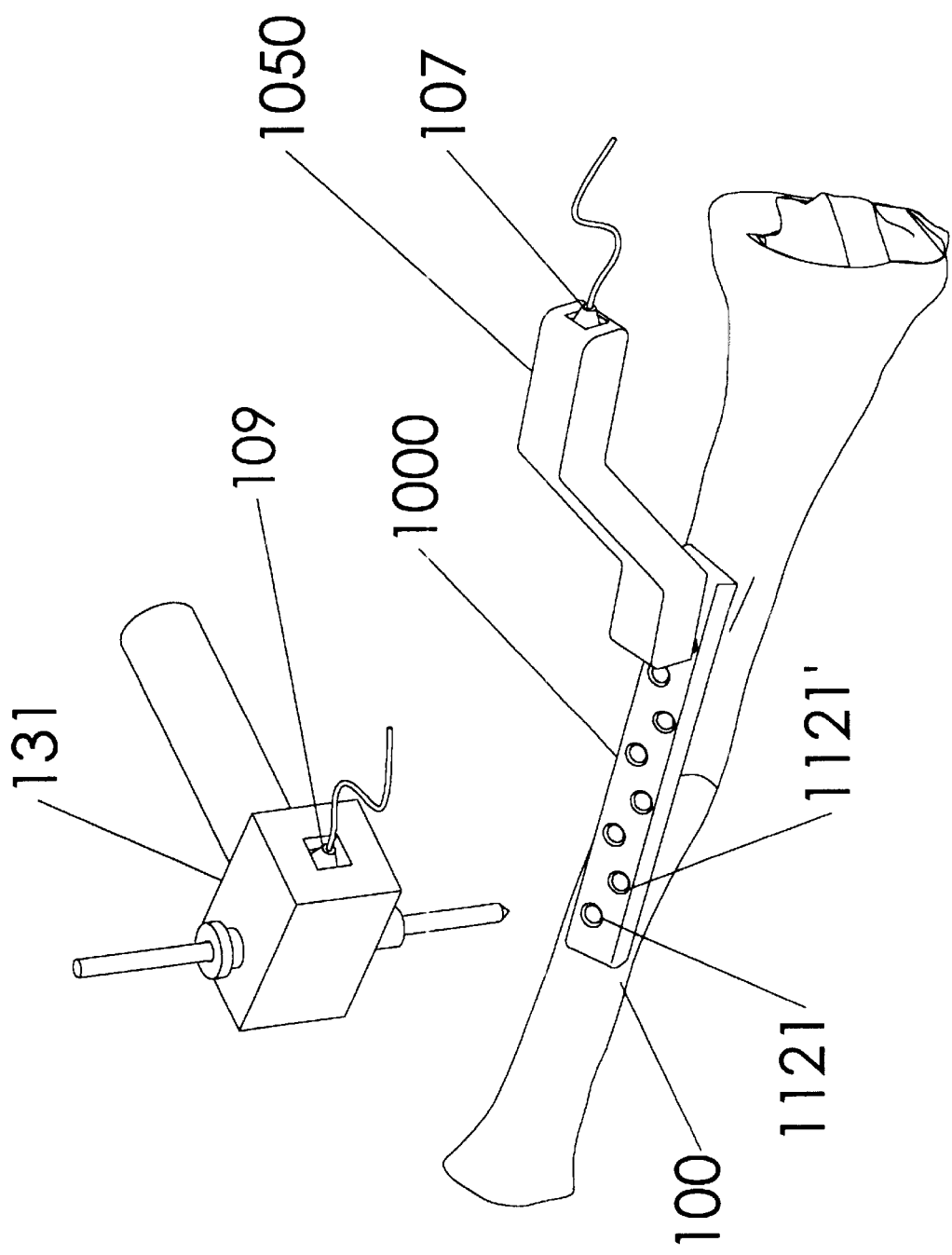
FIG. 10 is a perspective view of the disclosed system being used to secure a bone plate.
Figure 11:
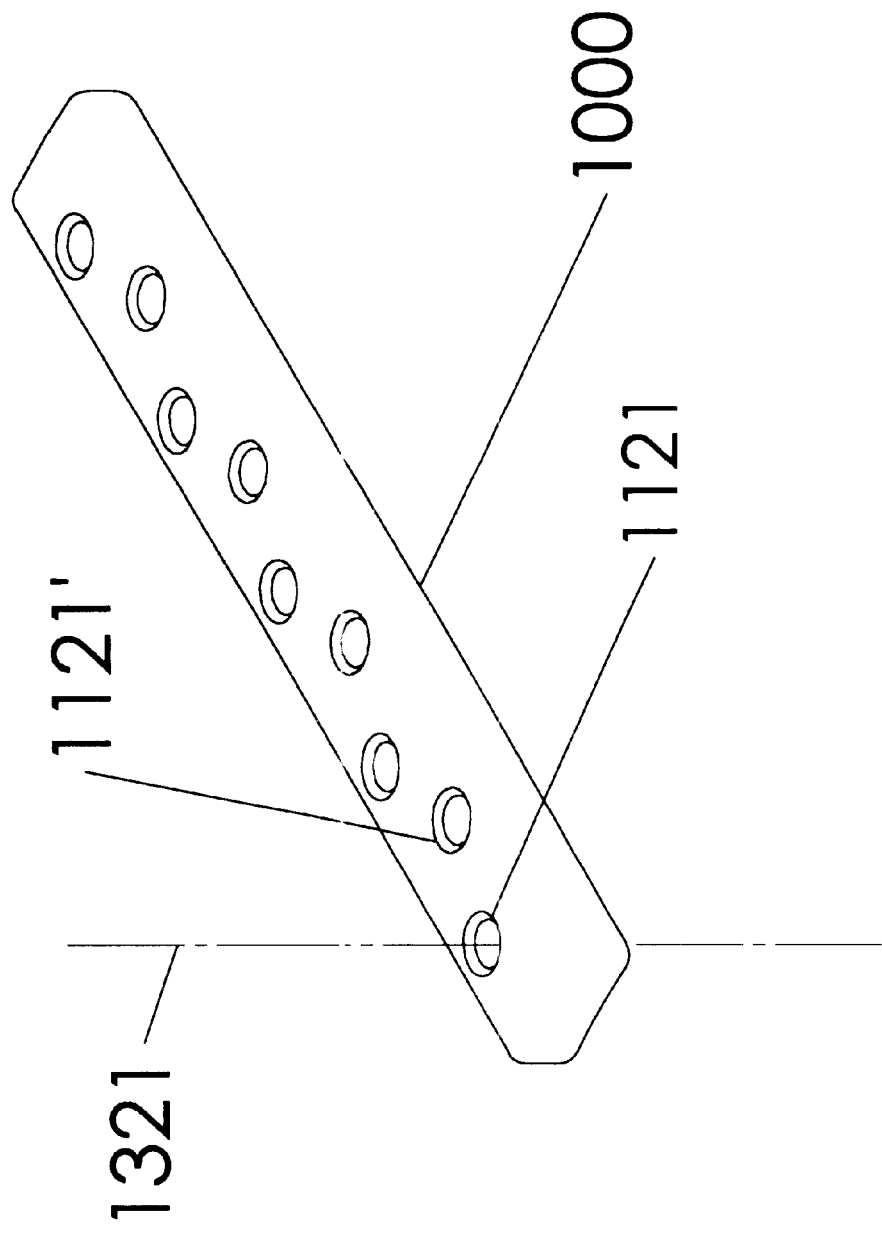
FIG. 11 is a perspective view of a bone plate

In another embodiment of the invention the system is used as a targeting means for insertion of screws through other internal fixation devices such as a bone plate or sliding hip screw into bone structures. Bone plates are attached to the external surface of the fractured bone to provide support and alignment during the healing process. As illustrated in FIG. 10, an attachment handle 1050 is temporarily fixed rigidly to the bone plate 1000, illustrated in FIG. 11. The receiver 107 is embedded within the handle 1050 and an additional receiver 109 is embedded or rigidly attached to a drill guide 131 as referenced in FIG. 1. The insertion of the bone screws to fix the bone plate 1000 would be in a manner similar to that described for the intramedullary nail. The location of each hole 1121 is registered in the computer for the particular plate 1000 being inserted or the hole location is determined using a calibration procedure.

After the bone plate 1000 has been positioned on the bone 100 either through an incision exposing the fractured bone or after inserting the plate 1000 through a small incision, the computer program prompts the surgeon to place the drill guide 131 at the specific hole location 1021. A stationary three dimensional cross-hair 111, representing the position of the axis 1321 of the desired transverse hole 1121 is displayed on the computer monitor. A second three-dimensional cross hair 112 is displayed on the monitor which represents the location and orientation of the drill guide axis relative to the axis of the desired transverse hole 1121. The surgeon then moves the drill jig until the guide's cross hairs 112 are aligned with the stationary cross hairs 111 on the monitor. The axis of the drill guide 532 is now aligned with the axis 1321 of the transverse hole of the plate. The drill guide is held firmly in this orientation or gently taped to set it in the bone 100, a drill 134 is inserted in the drill sleeve 133 and drilled through the nail hole 121. The drill 134 is removed and a screw 326 inserted to lock the plate 1000 with the bone 100. The computer is then programmed to proceed to the second hole 1121' and the procedure repeated. The procedure is repeated until all the holes have been drilled and screws inserted.

List of Components of the Invention

100 bone
101 Computer including monitor, cpu, keyboard, other devices
102 Electronic control unit and driver circuit
103 Wires connecting 101 with 102
104 Three axis transmitter
105 Coordinate axis of transmitter 104
106 Wires connecting 102 with 105
107 Receiver sensor in nail driver 125
108 Wires connecting 102 with 107
109 Receiver sensor in drill guide 131
110 Wires connecting 102 with 109
111 Stationary crosshairs representing nail hole axis 310
112 Crosshairs representing drill guide axis 520
120 Intramedullary nail
121 Locking hole in 120
122 Locking hole connected to hole 121 along axis 321 in 120
124 Proximal end of nail 120
125 Distal end of nail 120
130 Handle of drill guide
131 Drill guide with embedded receiver sensor 109
132 Drill guide hole
133 Inner drill sleeve
134 Outer drill sleeve
135 Drillbit
140 Nail driver
141 Attachment spacer
142 Interlocking shaft
143 Locking nut
201 Origin of transmitter coordinate axis 105
202 X-axis of coordinate axis 105
203 Y-axis of coordinate axis 105
204 Z-axis of coordinate axis 105
210 Receiver 107 coordinate axis
211 Origin of receiver coordinate axis 210
212 X-axis of coordinate axis 210
213 Y-axis of coordinate axis 210
214 Z-axis of coordinate axis 210
220 Receiver 109 coordinate axis
221 Origin of receiver coordinate axis 220
222 X-axis of coordinate axis 220
223 Y-axis of coordinate axis 220
224 Z-axis of coordinate axis 220
310 Offset coordinate axis of axis 210
321 axis of hole 121
322 Axis of hole 122
323 Axis of hole 123
324 Means of attachment (threads) at end 124
325 Alignment indentation on end 124
401 Handle of nail driver 140
402 Body of nail driver 140 along the longitudinal axis of nail 120
403 Longitudinal axis of nail driver segment 402
404 Cylindrical bore along axis 403
405 End of segment 402 for attachment with 141
406 Alignment protrusion on end 405 for alignment with attachment spacer 141
409 Cavity for wire 108
410 End of 141 for attachment with proximal end 124 of nail 120
411 Protrusion on end 410 for mating with indentation 325 on proximal nail end 124
412 End of 141 for attachment with nail driver end 405
413 Indentation on end 412 for mating with protrusion 406
414 Threaded internal bore of locking nut 143
415 Longitudinal bore through spacer 141
421 Threaded end of 142 for attachment with 324
422 Threaded end of 142 for attachment with 143
423 Connecting member of 142 connecting end 411 with end 412
520 Coordinate axis of center of drill hole 132 and coincident with axis 521
521 Longitudinal axis of drill hole 132
525 Bore within drill guide 131 for drill sleeve 133
531 End section of drill sleeve 133
532 Longitudinal section of drill sleeve 133
533 Internal bore of drill sleeve 133
541 End section of drill sleeve 134
542 Longitudinal section of drill sleeve 134
543 Internal bore of drill sleeve 134
700 Alignment tool
705 end of alignment tool intended to coincide with drill guide bore 533 or drill sleeve bore
710 central section of alignment tool 700
715 end of alignment tool 700 intended to coincide with nail hole 121–122 along axis 321
721 longitudinal axis of alignment tool 700
805 Probe head with embedded receiver 107
810 Probe shank attached to probe head and containing wire 108
812 Stop member
813 Central bore of stop member 812
814 Stop member locking screw
905 Probe extension
910 Probe extension prong

What is claimed is:
1. An apparatus for use in securing a first member to a second member, wherein said second member is hidden from visual observation within a third member comprising:
  A. a first member, said first member having a first receiver and at least one connector receiving means for receiving a connector,
  B. a guide member, said guide member having one of a second receiver or a transmitter and carrying said connector;
  C. electronics for positioning and orienting said guide member relative to said first member connector receiving means, said device having;
    (a) a direct current magnetic field transmitter;
    (b) at least one magnetic field receiver for receiving said transmitted direct current magnetic fields;
    (c) power means for supplying direct current electrical signals to said magnetic field transmitter to create said transmitted direct current magnetic fields;
    (d) receiver electronics for measuring, and converting out-put signals from said magnetic field receiver into position and orientation measurements,

(e) programmed computer, said programmed computer having a visual display member, said output signals from said receiver electronics being converted into position and orientation measurements and visually displayed on said computer visual display member, whereby the relative position and orientation of said first member connector receiving means relative to said guide member is determined.

2. The device of claim 1, where said device consists of a single transmitter and a plurality of receivers.

3. The device of claim 1, wherein said first member is an implant for bone stabilization, and said third member is a bone.

4. The device of claim 1, wherein said receiver electronics are provided by said programmed computer.

5. The device of claim 4, said implant having a near end and a far end, and further comprising a support member, said support member being releasably secured to said near end of said implant, one of said receiving means being fixed to said implant by being secured to said support member, said connector receiving means being positioned proximate the far end of said implant.

6. The device of claim 1, where in said transmitter for transmitting direct current magnetic fields comprises a core and a multiplicity of roughly orthogonal antenna axis wire windings.

7. The device of claim 1 wherein said receiving means for receiving said transmitted direct current magnetic fields comprises a multiplicity of roughly orthogonal antennae axes that are sensitive to transmitted direct current magnetic fields.

8. The device of claim 1 wherein said transmitter for transmitting direct current magnetic fields comprises a core and a multiplicity of roughly orthogonal antenna axis wire windings, and said receiving means for receiving said transmitted direct current magnetic fields comprises a multiplicity of roughly orthogonal antennae axes that are sensitive to transmitted direct current magnetic fields.

9. The method of calibrating and determining the fixed offset distance and orientation between at least two positions relative to third position, where the first position is the location of a magnetic field transmitter, comprising the steps of:

1—transmitting a predetermined magnetic field from said first position,

2—positioning a movable guide element to a first of said at least two positions, said movable guide element having means for receiving said predetermined magnetic field, 3—receiving said predetermined magnetic field at said first of said at least two positions, 4—receiving said predetermined magnetic field at a second of said at least two positions, 5—computing the fixed distance and orientation offset between said first position and said second position of said at least two positions, 6—storing in a computer data memory, the computed data representing said fixed distance and orientation offset between said first position and said second position of said at least two positions, whereby said movable guide member at said second of said at least two positions can be reproducably located relative to said first of said at least two positions, by means of magnetic fields transmitted from said first position.

10. The method of claim 9, further comprising the steps of determining the fixed offset distance and orientation of a plurality of offset positions relative to a single predetermined position, by repeating steps 1 to 6, for each of said plurality of offset positions.

11. The method of claim 9, further comprising a mounting member, a receiving means fixed to said mounting means, said mounting member and receiving means being positioned within said first device, and a securing member, said securing member locking said receiving means within said first device.

* * * * *